(12) United States Patent
Calogeropoulou et al.

(10) Patent No.: US 8,097,752 B2
(45) Date of Patent: Jan. 17, 2012

(54) ANTIPROTOZOAL RING-SUBSTITUTED PHOSPHOLIPIDS

(75) Inventors: Theodora Calogeropoulou, Attiki (GR); Maria Koufaki, Athens (GR); Nikolaos Avlonitis, Attiki (GR); Alexandros Makriyannis, Watertown, MA (US)

(73) Assignee: MAKScientific, LLC, Mystic, CT (US)

( * ) Notice: Subject to any disclaimer, the term of this patent is extended or adjusted under 35 U.S.C. 154(b) by 1176 days.

(21) Appl. No.: 10/531,324

(22) PCT Filed: Oct. 29, 2003

(86) PCT No.: PCT/US03/34225
§ 371 (c)(1),
(2), (4) Date: Dec. 20, 2005

(87) PCT Pub. No.: WO2004/041167
PCT Pub. Date: May 21, 2004

(65) Prior Publication Data
US 2006/0105998 A1 May 18, 2006

Related U.S. Application Data

(60) Provisional application No. 60/422,383, filed on Oct. 30, 2002.

(51) Int. Cl.
| | |
|---|---|
| C07D 295/037 | (2006.01) |
| C07D 211/06 | (2006.01) |
| C07F 9/38 | (2006.01) |
| C07C 209/00 | (2006.01) |
| A61K 31/14 | (2006.01) |
| A61K 31/44 | (2006.01) |
| A61K 31/5375 | (2006.01) |
| A61K 31/662 | (2006.01) |
| A61P 33/02 | (2006.01) |

(52) U.S. Cl. .......... 562/8; 562/11; 562/14; 544/84; 544/108; 546/184; 514/76; 514/231.5; 514/315; 514/642

(58) Field of Classification Search ............ 558/166; 554/84; 514/77, 76, 231.5, 315, 642; 544/166, 544/84, 108; 562/8, 11, 14; 546/184
See application file for complete search history.

(56) References Cited

U.S. PATENT DOCUMENTS

| | | | |
|---|---|---|---|
| 5,087,721 A * | 2/1992 | Counsell et al. | 558/166 |
| 5,436,234 A | 7/1995 | Eibl | |
| 5,776,915 A * | 7/1998 | Peterson et al. | 514/77 |
| 5,977,314 A | 11/1999 | Landry et al. | |
| 5,980,915 A | 11/1999 | Eibl et al. | |

(Continued)

FOREIGN PATENT DOCUMENTS

DE     BE 2359245 A1 *  6/1974

(Continued)

OTHER PUBLICATIONS

Freshney et al.,Culture of Animal Cells, A Manual of Basic Technique, Alan R. Liss, Inc., 1983, New York, p. 4.*

(Continued)

*Primary Examiner* — Venkataraman Balasubramanian
(74) *Attorney, Agent, or Firm* — Alix, Yale & Ristas, LLP

(57) ABSTRACT

Disclosed are novel ring containing phospholipids represented by the structural formula A-X—PO$_3$—W and physiologically acceptable salts thereof and a process for the preparation of these compounds. The compounds can be used for the treatment of protozoal diseases and especially leishmaniasis.

22 Claims, 3 Drawing Sheets

U.S. PATENT DOCUMENTS

| | | |
|---|---|---|
| 6,254,879 B1 | 7/2001 | Eibl et al. |
| 6,344,576 B1 | 2/2002 | Eibl |

FOREIGN PATENT DOCUMENTS

| | | |
|---|---|---|
| EP | 0 507 337 | 10/1992 |
| WO | WO 9855533 A1 * | 12/1998 |
| WO | WO 99/09037 | 2/1999 |

OTHER PUBLICATIONS

Stuart K. et al., Journal of Clinical Investigation (2008), 118(4), 1301-1310.*

Anderson A.C., Drug Discovery Today (2005), 10(2), 121-128.*

Sing S. et al., J. Infect. Chemother., (2004), 10, 307-315.*

Yamaguchi et al., Macromolekulare Chemie, (1980), 190(5), 1195-11205: CA 111:58423, 1989.*

Fong et al., Lipids 12(10), 857-62, 1977; CA 88:17757, 1978(CAPLUS Abstract provided).*

D. Hart et al, "Ether Lipid (Alkylphospholipid) Analogs as Antileishmanial Drugs", *Drugs of Today,* vol. 34, Suppl. F., 1998, pp. 117-131, XP009054682.

N. Avlonitis et al, "Antileishmanial Ring-Substituted Ether Phospholipids", *Journal of Medicinal Chemistry,* vol. 46, 2003, pp. 755-767, XP002383657.

Supplementary European Search Report for application No. 03779386 dated Jun. 20, 2006.

* cited by examiner

Figure 1 Cytotoxicity of ether phospholipids on THP-1 cell line

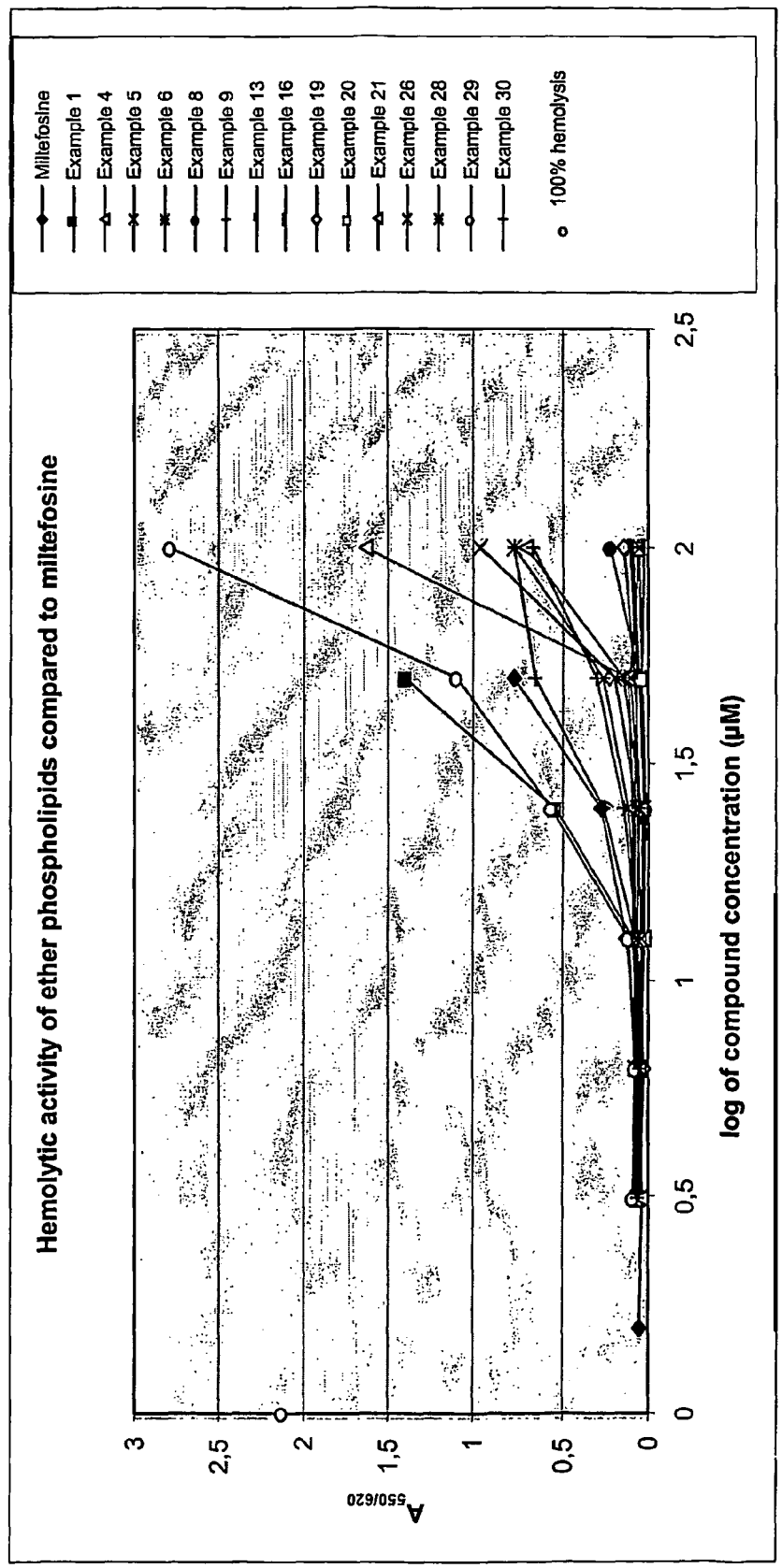
Figure 3 Hemolysis of red blood cells by ether phospholipids compared to miltefosine

ANTIPROTOZOAL RING-SUBSTITUTED PHOSPHOLIPIDS

This application is the U.S. National Stage of International Application No. PCT/US2003/034225, filed Oct. 29, 2003, which claims the benefit of U.S. Provisional Application No. 60/422,383, filed Oct. 30, 2002, the contents of each of which are incorporated herein by reference in their entirety.

BACKGROUND OF THE INVENTION

Leishmaniasis is a protozoan parasitic disease endemic in 88 countries, which causes considerable morbidity and mortality. At least 20 species of *Leishmania* can be transmitted by sandfly bites, originating cutaneous, diffuse cutaneous, mucocutaneous and visceral leishmaniasis in humans, dogs and various wild vertebrate hosts. The estimated yearly incidence is 1-1.5 million cases of cutaneous leishmaniasis and 500,000 cases of visceral leishmaniasis. The population at risk is estimated at 350 million people with an overall prevalence of 12 million. Increasing risk factors are making leishmaniasis a growing public health concern for many countries around the world.

The drugs most commonly used to treat leishmaniasis are the pentavalent antimonials sodium stibogluconate (Pentostam) and meglumine antimonate (Glucantime). Antimonial chemotherapy requires high dose regimens with long treatment courses using parenteral administration. Second-line drugs, used in instances of antimonial-treatment failure, include amphotericin B (AMB), paromomycin (aminosidine), and pentamidine. However, all of these drugs are far from satisfactory due to unacceptable side effects at effective doses. The recently developed liposomal formulation of amphotericin B (AmBisome™) showed good curative rates for antimony unresponsive cases of mucocutaneous leishmaniasis however, drug administration is technically difficult and treatment costs are prohibitively expensive.

The spreading resistance of the parasite towards the standby antimonial drugs, the high toxicity of most drugs in use, and the emergence of *Leishmania*/HIV co-infection as a new disease entity has triggered a continuous search for alternative therapies. Visceral leishmaniasis caused by *L. infantum* has emerged as an AIDS-associated opportunistic infection, particularly in southern Europe.

In recent years, alkyllysophospholipid analogues (ALPs) have received considerable interest due to their antineoplastic and immunomodulatory properties. Extensive structure-activity relationship studies on a variety of ALPs showed that a long alkyl chain and a phosphocholine moiety may represent the minimal structural requirements for sufficient antineoplastic effects of ether lipid analogues. This finding led to the synthesis of the alkylphosphocholines (APCs). Within the alkyl chain homologs, hexadecylphosphocholine (HePC) has therapeutically useful antitumor activity and was approved in 1992 as a drug in Germany for the topical treatment of metastasized mammary carcinoma.

Several in vitro and in vivo studies demonstrated that alkylphosphocholines including HePC, and alkylglycerophosphocholines such as edelfosine, ilmofosine and SRI-62,834 possess antileishmanial activity. Hexadecylphosphocholine was reported to be highly effective in treating mice infected with visceral leishmaniasis while oral treatment with miltefosine was 600-fold more effective than the subcutaneous administration of pentostam. On the basis of these promising observations HePC (miltefosine) was evaluated in phase I and II clinical trials as oral therapy for Indian visceral leishmaniasis while phase III clinical trials are currently ongoing. Cure rates of 88% to 100% were obtained using doses of 100-150 mg/day for 28 days. These results encouraged studies on the efficacy of miltefosine treatment for cutaneous leishmaniasis in the New World and currently phase II studies are being conducted. In a phase I study, the cure rate with miltefosine at doses of 100-150 mg for 3 weeks was 94%. In the various clinical trials, the main side effects associated with miltefosine were gastrointestinal with the most common being moderate vomiting and diarrhea. Transient elevation of transaminases or urea/serum creatinine was noted in a number of patients and decreased under continued treatment. Although the toxicity associated with miltefosine sounds milder than that of some parenteral therapies, gastrointestinal symptoms could be of more consequence in severely ill patients, such as those who are malnourished or dehydrated. In addition, treatment of pregnant women is contraindicated because of miltefosine's teratogenic properties in animals. Furthermore, miltefosine has a very long half-life and low therapeutic ratio and a course of treatment leaves a subtherapeutic level in the blood for several weeks. These drug characteristics might be expected to encourage development of resistance. Additionally, miltefosine was shown to be only temporarily effective in HIV co-infected patients in Europe. Therefore, a need exists for new phospholipids in the treatment of protozoal diseases and especially leishmaniasis that will not cause significant adverse side effects.

U.S. Pat. No. 5,436,234 discloses compounds of the general formula:

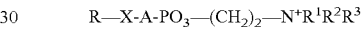

R—X-A-PO$_3$—(CH$_2$)$_2$—N$^+$R$^1$R$^2$R$^3$

Wherein R is a erucyl, brassidyl or nervonyl radical, R$^1$, R$^2$ and R$^3$ are, independently of one another, straight-chained, branched or cyclic saturated or unsaturated alkyl radicals containing up to 4 carbon atoms, which can also contain a hydroxyl group, and wherein two of these radicals can also be connected together to form a ring, A is a valency bond or a radical of one of the formulae:

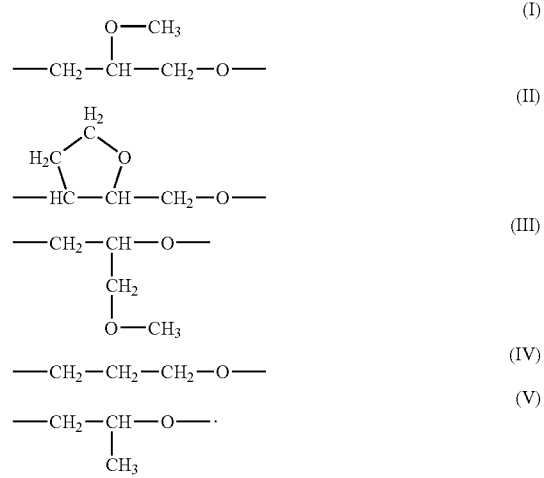

And X is an oxygen atom when A is preferably a valency bond. Compounds of the general formula R—X-A-PO$_3$—(CH$_2$)$_2$—N$^+$R$^1$R$^2$R$^3$ and pharmaceutical compositions containing them can be used for the treatment of protozoal and fungal diseases, autoimmune diseases and bone marrow damage.

U.S. Pat. No. 6,254,879 which is continuation-in part of application Ser. No. 08/469,779 now U.S. Pat. No. 5,980,915 discloses a new pharmaceutical agent for oral or topical administration in the treatment of protozoal diseases, in particular of leishmaniasis which contains as the active substance one or several compounds of the general formula $$R^1-PO_4-CH_2CH_2-N^+R^2R^3R^4$$

in which $R^1$ is a saturated or monounsaturated or polyunsaturated hydrocarbon residue with 12 to 20 C atoms.

U.S. Pat. No. 6,344,576 relates to phosphor-lipid compounds of formula (I)

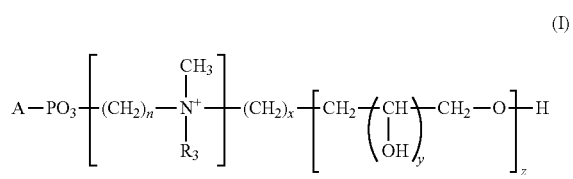

having solubilizing activity for water-insoluble or poorly water soluble active agents and their use in the delivery of active agents to cells and in the treatment of diseases, i.e. cancer and protozoal diseases.
in which A

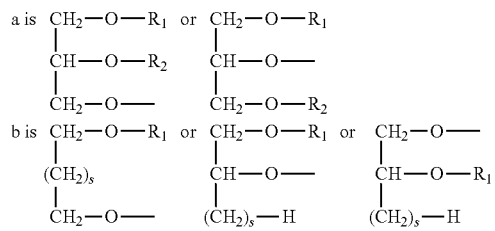

where $R_1$ and $R_2$ are, independently of one another, hydrogen, a saturated or unsaturated acyl or alkyl radical which can optionally be branched or/and substituted, where the total of the carbon atoms in the acyl and alkyl is 16 to 44 C atoms.

SUMMARY OF THE INVENTION

One aspect of this invention pertains to novel ring containing phospholipids and use thereof in treating protozoal diseases such as leishmaniasis, trypanosomiasis, malaria, toxoplasmosis, babeosis, amoebic dysentery and lambliasis. The compounds of the present invention comprise phospholipids of the general formula A-X—PO$_3$—W.

Another aspect of this invention relates to a method of preparing said compounds.

A further aspect of this invention relates to method for treating protozoal infections includes administering an effective infection-combating amount of a compound of the present invention in a therapeutic manner.

A better understanding of the invention will be obtained from the following detailed description of the article and the desired features, properties, characteristics, and the relation of the elements as well as the process steps, one with respect to each of the others, as set forth and exemplified in the description and illustrative embodiments.

BRIEF DESCRIPTION OF THE DRAWINGS

FIG. 3 shows the hemolytic activity of selected examples with respect to miltefosine.

DETAILED DESCRIPTION OF THE INVENTION

Figure 1:
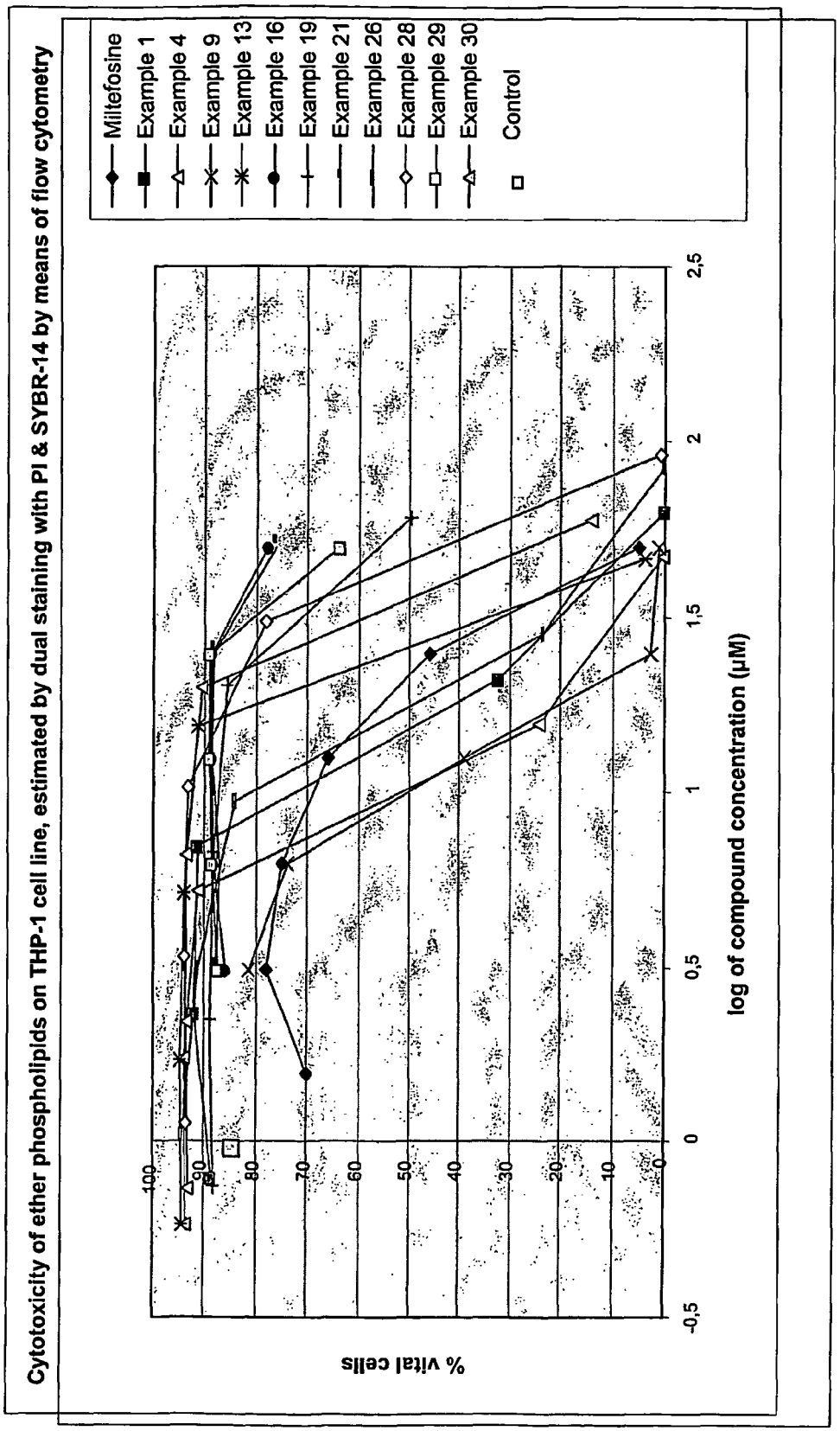
FIG. 1 is a graph illustrating the percentage of live THP1 cells in the presence of a different concentrations of some inventive compounds.
Figure 2:
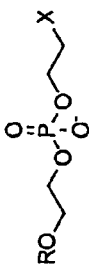
FIG. 2 illustrates some inventive compounds.

The present invention relates to new ring-containing phospholipids of the general formula A-X—PO$_3$—W their stereoisomers and geometrical isomers and physiologically acceptable salts thereof, as well as pharmaceutical compositions containing them.

The phospholipid compounds of the present invention of general formula A-X—PO$_3$—W in the residue A contain rings of different sizes and types at positions of the phospholipid structure which are not encountered in prior art compounds. The prior art compounds bear only straight or branched alkyl chain substituents in the residue A apart from U.S. Pat. No. 5,436,234 in which there is a tetrahydrofuranyl substituent in residue A. However, the prior art compounds are not covered by the formulae of the compounds claimed in the present invention.

The novel ring-substituted phospholipids of this invention are represented by the general formula A-X—PO$_3$—W.

A comprises a radical selected from one of the formulae Y, YR$^1$, R$^1$Y, R$^1$YR$^4$, R$^1$OY, YOR$^1$, R$^1$YOR$^2$ or R$^1$OYOR$^2$. Advantageously A comprises YR$^1$, R$^1$YOR$^2$ or R$^1$OYOR$^2$ W comprises a radical of the formulae R$^3$Q or a C4 to C7 non-aromatic heterocycle containing a nitrogen heteroatom wherein said heterocycle comprising at least one heteroatom independently selected from nitrogen, oxygen, sulfur and combinations thereof, and wherein said heterocycle can be substituted with one or more substituent groups. Advantageously, the substituent groups are independently selected from hydroxyl, halogen, alkyl, cycloalkyl, aryl, alkoxy, alkoxycarbonyl, alkylthio or amino.

Y comprises a carbocyclic ring, a carbocyclic ring comprising at least one substituent group, a fused bicyclic ring system, a fused bicyclic ring system comprising at least one substituent group, a bridged bicyclic ring system, a bridged bicyclic ring system comprising at least one substituent group, a bridged tricyclic ring system, a bridged tricyclic ring system comprising at least one substituent group, a heterocyclic ring, a heterocyclic ring comprising at least one substituent group, an aromatic system or an aromatic system comprising at least one substituent group, a heteroaromatic system or a heteroaromatic system comprising at least one substituent group.

X comprises a valency bond, a methylene group (—CH$_2$—) or a heteroatom selected from nitrogen, oxygen, sulfur. Advantageously the heteroatom is an oxygen atom.

R$^1$ comprises any possible member selected from a carbocyclic ring having about 3 to about 7 ring members, a heterocyclic ring having about 4 to about 7 ring members, an aromatic ring having about 5 to about 7 ring members, a heteroaromatic ring having about 5 to about 7 ring members, or any above group comprising a substituent group on at least one available ring atom, an about C3 to about C20 saturated or unsaturated, straight or branched, aliphatic hydrocarbon chain, an about C3 to about C20 saturated or unsaturated, straight or branched, aliphatic hydrocarbon chain comprising one or more independently chosen heteroatoms, an about C3 to about C20 saturated or unsaturated, straight or branched, aliphatic hydrocarbon chain comprising at least one independently chosen possible member selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; or any above member comprising a substituent group on at least one available ring atom, or any above about C3 to about C20 hydrocarbon chain having at least one independently chosen substituent group. Advantageously, the substituent groups for the about C3 to about C20 hydrocarbon chain are independently selected from hydroxyl, halogen, alkyl, cycloalkyl, aryl, alkoxy, alkoxycarbonyl, alkylthio or amino.

$R^2$ comprises any possible member selected from a carbocyclic ring having about 3 to about 7 ring members, a heterocyclic ring having about 4 to about 7 ring members, an aromatic ring having about 5 to about 7 ring members, a heteroaromatic ring having about 5 to about 7 ring members; any above group comprising a substituent group on at least one available ring atom, an about C2 to about C5 saturated or unsaturated, straight or branched, aliphatic hydrocarbon chain, an about C2 to about C5 saturated or unsaturated, straight or branched, aliphatic hydrocarbon chain comprising one or more independently chosen heteroatoms, an about C2 to about C5 saturated or unsaturated, straight or branched, aliphatic hydrocarbon chain comprising at least one independently chosen possible member selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; or any above member comprising a substituent group on at least one available ring atom, or any above about C2 to about C5 hydrocarbon chain having at least one independently chosen substituent group.

Advantageously, $R^2$ comprises a C2 saturated or unsaturated alkyl or alkenyl, a C2 saturated or unsaturated alkyl or alkenyl which can be substituted with one or more substituents selected from hydroxyl, halogen, alkyl, cycloalkyl, aryl, alkoxy, alkoxycarbonyl, alkylthio and amino.

$R^3$ comprises any possible member selected from a carbocyclic ring having about 3 to about 9 ring members, a heterocyclic ring having about 4 to about 9 ring members, an aromatic ring having about 5 to about 9 ring members, a heteroaromatic ring having about 5 to about 9 ring members; any above group comprising a substituent group on at least one available ring atom, an about C2 to about C5 saturated or unsaturated, straight or branched, aliphatic hydrocarbon chain, an about C2 to about C5 saturated or unsaturated, straight or branched, aliphatic hydrocarbon chain comprising one or more independently chosen heteroatoms, an about C2 to about C5 saturated or unsaturated, straight or branched, aliphatic hydrocarbon chain comprising at least one independently chosen possible member selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; or any above member comprising a substituent group on at least one available ring atom, or any above about C2 to about C5 hydrocarbon chain having at least one independently chosen substituent group.

Advantageously $R^3$ comprises a C2 saturated or unsaturated alkyl or alkenyl, a C2 saturated or unsaturated alkyl or alkenyl which can be substituted with one or more substituents selected from hydroxyl, halogen, alkyl, cycloalkyl, aryl, arylalkyl, alkoxy, alkoxycarbonyl, alkylthio and amino or a C3 to C8 cycloalkyl which is bonded at C1 to the oxygen and at C2 to Q.

$R^4$ comprises any group independently selected from $R^1$ or $R^2$.

Q comprises an ammonium group, wherein said ammonium group can be substituted one or more times with a C1 to C6 alkyl radical, or comprises a C3 to C7 heterocycle containing a nitrogen heteroatom which is bonded to the $R^3$ group, wherein said heterocycle can contain one or more heteroatoms independently selected from nitrogen, oxygen, sulfur and combinations thereof, and wherein said heterocycle can be substituted with one or more substituent groups, a heterobicyclic ring containing a nitrogen heteroatom which is bonded to the $R^3$ group, wherein said heterobicyclic ring can contain one or more heteroatoms independently selected from nitrogen, oxygen, sulfur and combinations thereof, and wherein said heterobicyclic ring can be substituted with one or more substituent groups, a heterotricyclic ring containing a nitrogen heteroatom which is bonded to the $R^3$ group, wherein said heterotricyclic ring can contain one or more heteroatoms independently selected from nitrogen, oxygen, sulfur and combinations thereof, and wherein said heterotricyclic ring can be substituted with one or more substituent groups. Advantageously the substituent groups are independently selected from hydroxyl, halogen, alkyl, cycloalkyl, aryl, alkoxy, alkoxycarbonyl, alkylthio or amino.

Examples of preferred residue $R^1$ comprise a C5 to C18 alkylidene group or C5 to C18 alkyl group and most preferred pentylidene, undecylidene, dodecylidene, tetradecylidene, and hexadecylidene group or pentyl, undecyl, dodecyl, tetradecyl and hexadecyl groups.

Examples of preferred Y residue comprise a C3 to C6 carbocyclic ring, a substituted carbocyclic ring, a bridged tricyclic ring system or a substituted bridged tricyclic ring system an aromatic ring and most preferred are cyclohexyl or adamantyl or phenyl. A C2 saturated alkyl is most preferred for $R^2$ and $R^3$. Oxygen is preferred for X. Trimethylammonium, or N-methylmorpholinio or N-methylpiperidinio is most preferred for Q.

The inventive compounds include any and all isomers and stereoisomers, as well as their addition salts, particularly their pharmaceutically acceptable addition salts. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in prior art compositions or that are otherwise not necessary to the achievement of the function and/or objectives of the present invention.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 16 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated. Unless otherwise specifically limited, an alkyl group can be unsubstituted, singly substituted or, if possible, multiply substituted, with substituent groups in any possible position. Unless otherwise specifically limited, a cyclic alkyl group includes monocyclic, bicyclic, tricyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N(alkyl)$_2$. Unless otherwise specifically limited di-alkylamino includes cyclic amine compounds such as piperidine and morpholine.

Unless otherwise specifically defined, an aromatic ring is an unsaturated ring structure having about 5 to about 7 ring members and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl or naphthyl. The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused or bridged rings that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include, Dimethyl-bicyclo[3,1,1]heptane, bicyclo[2,2,1]heptadiene, decahydronaphthalene and bicyclooctane.

Unless otherwise specifically defined, a carbocyclic ring is a non-aromatic ring structure, saturated or unsaturated, having about 3 to about 8 ring members that includes only carbon as ring atoms, for example, cyclohexadiene or cyclohexane. The carbocyclic ring can be unsubstituted, singly substituted or, if possible, multiply substituted, with substituent groups in any possible position.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members that has carbon atoms and one or more heteroatoms, including oxygen, nitrogen and/or sulfur, as ring atoms, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused or bridged rings that include carbon and one or more heteroatoms, including oxygen, nitrogen and/or sulfur, as ring atoms. The heterobicyclic ring structure is saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include tropane, quinuclidine and tetrahydro-benzofuran.

Unless otherwise specifically defined, a heterocyclic ring is a saturated or unsaturated ring structure having about 3 to about 8 ring members that has carbon atoms and one or more heteroatoms, including oxygen, nitrogen and/or sulfur, as ring atoms, for example, piperidine, morpholine, piperazine, pyrrolidine, thiomorpholine, tetrahydropyridine, and their derivatives. The heterocyclic ring can be unsubstituted, singly substituted or, if possible, multiply substituted, with substituent groups in any possible position.

Unless otherwise specifically defined, a heterotricyclic ring structure comprises 3 rings that may be fused, bridged or both fused and bridged, and that include carbon and one or more heteroatoms, including oxygen, nitrogen and/or sulfur, as ring atoms. The heterotricyclic ring structure can be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include 2,4,10-trioxaadamantane, tetradecahydro-phenanthroline.

Unless otherwise specifically defined, a heteropolycyclic ring structure comprises more than 3 rings that may be fused, bridged or both fused and that include carbon and one or more heteroatoms, including oxygen, nitrogen and/or sulfur, as ring atoms. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, 5-norbornene-2,3-dicarboximide.

Unless otherwise specifically defined, the term "phenacyl" refers to the general formula -phenyl-acyl.

Unless otherwise specifically defined, a polycyclic ring structure comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position and may be substituted or unsubstituted. The individual rings may or may not be of the same type. Examples of tricyclic ring structures include fluorene and anthracene.

Unless otherwise specifically limited the term substituted means substituted by a below described substituent group in any possible position. Substituent groups for the above moieties useful in the invention are those groups that do not significantly diminish the biological activity of the inventive compound. Substituent groups that do not significantly diminish the biological activity of the inventive compound include, for example, H, halogen, $N_3$, NCS, CN, $NO_2$, $NX_1X_2$, $OX_3$, OAc, O-acyl, O-aroyl, OalkylOH, OalkylN$X_1X_2$, NH-acyl, NH-aroyl, NHCOalkyl, CHO, $CF_3$, $COOX_3$, $SO_3H$, $PO_3X_1X_2$, $OPO_3X_1X_2$, $SO_2NX_1X_2$, $CONX_1X_2$, alkyl, alcohol, alkoxy, alkylmercapto, alkylamino, di-alkylamino, sulfonamide, thioalkoxy, aryl, substituted aryl, heteroaryl, substituted heteroaryl or methylene dioxy when the substituted structure has two adjacent carbon atoms, wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, hydroxylower-alkyl, or alkyl-$NX_1X_2$. Unless otherwise specifically limited a substituent group may be in any possible position.

The present invention also pertains to methods for treating protozoal diseases such as leishmaniasis, trypanosomiasis, malaria, toxoplasmosis, babeosis, amoebic dysentery and lambliasis. The method comprises administering an effective infection-combating amount of a compound of the present invention in a therapeutic manner. In one embodiment, an effective dose includes a sufficient amount of one stereoisomer or mixture of stereoisomers where all stereoisomers of said compound possess antiprotozoal properties. In an alternate embodiment, where only one stereoisomer of a compound possesses significant antiprotozoal properties an effective dose comprises a sufficient amount of the pure antiprotozoal stereoisomer.

The compounds of the present invention can be administered topically, enterally and parenterally in liquid or solid form.

The invention further relates to a method of preparing said compounds. According to the invention the compounds of formula A-X—$PO_3$—W are synthesized in the following way:

i) Treating the appropriate alcohol A-OH in which A is defined above with phosphorus oxychloride in an organic solvent such as tetrahydrofuran for example in the presence of an organic base, such as triethylamine for example to afford the corresponding phosphoric acid derivative after hydrolysis.

ii) Treating the phosphoric acid said above with 1-(mesitylen-2-sulfonyl)-3-nitro-1H-1,2,4-triazole or 2,4,6-triisopropylbenzenesulfonyl chloride in an organic base, such as pyridine for example followed by the addition of the appropriate alcohol W—OH in which W is defined above and heating the resulting mixture to provide after hydrolysis the phospholipid A-X—$PO_3$—W.

The invention will be further illustrated by the following non-limiting examples.

EXEMPLIFICATION

Synthetic Procedures

General Methods

All reactions were carried out under scrupulously dry conditions. NMR spectra of all new compounds were recorded on a Bruker AC 300 spectrometer operating at 300 MHz for $^1$H, 75.43 MHz for $^{13}$C, and 121.44 MHz for $^{31}$P. $^1$H NMR spectra are reported in units δ with $CHCl_3$ resonance at 7.24 ppm used as the chemical shift resonance. $^{13}$C NMR shifts are expressed in units relative to $CDCl_3$ at 77.00 ppm, while $^{31}$P NMR spectra are reported in units of δ relative to 85% $H_3PO_4$ used as an external standard. Silica gel plates Merck $F_{254}$) were used for thin-layer chromatography. Chromatographic purification was performed with silica gel (200-400 mesh).

General Procedure for the Preparation of Ether Phospholipids.

To a solution of phosphorus oxychloride (0.09 mL, 1 mmol) and triethylamine (0.25 mL, 1.8 mmol) in dry THF (5 mL) was added dropwise at 0° C. a solution of the corresponding alcohol (1 mmol) in dry THF (7 mL). The resulting mixture was stirred for 2 h at room temperature and subsequently hydrolyzed by the addition of water (3 mL). After 1 h of stirring at room temperature, the reaction mixture was diluted with water and the aqueous layer was extracted with ethyl acetate and dichloromethane. The combined organic extracts were washed with brine, dried with anhydrous $Na_2SO_4$ and the solvent was evaporated in vacuo to afford the corresponding phosphoric acid derivative, which was transformed to the pyridinium salt by the addition of 7 mL of anhydrous pyridine and stirring for 2 h at 40° C. After cooling the solvent was evaporated in vacuo and pyridine (5 mL) was added to the residue. To the resulting solution was added dropwise with cooling, a solution of 1-(mesitylen-2-sulfonyl)-3-nitro-1H-1,2,4-triazole (MSNT) (0.593 g, 2 mmol) or 2,4,6-triisopropylbenzenesulfonyl chloride (TIPS-Cl) (0.606 g, 2 mmol) in dry pyridine (2 mL) followed by the addition of choline chloride (0.210 g, 1.5 mmol) or N-(2-hydroxyethyl)-N-methylpiperidinium bromide (0.448 g, 1.5 mmol) or N-(2-hydroxyethyl)-N-methylmorpholinium bromide (0.452 g, 1.5 mmol). The reaction mixture was stirred at 40° C. for 48-56 hours. After cooling, the mixture was hydrolyzed by the addition of $H_2O$ (2 mL) and 2-propanol (7 mL) and stirred for 1 h at room temperature. The solvents were evaporated in vacuo and the resulting crude solid was purified by gravity column chromatography using initially $CH_2Cl_2$/MeOH/25% $NH_4OH$ (60/50/5) and subsequently MeOH/25% $NH_4OH$ (95/5) and the solvents were evaporated in vacuo. The residue was diluted with $CHCl_3$ and filtered through a pore membrane (0.5 μM, FH Millipore). After evaporation of the solvent the desired product was obtained.

Example 1

1-{2-{[(4-Dodecylidenecyclohexyloxy)ethyloxy]hydroxyphosphinyloxy}ethyl}-N,N,N-trimethylammonium inner salt The general procedure described above using 2-(4-dodecylidenecyclohexyloxy)ethanol, TIPS-Cl and choline chloride afforded the compound named above (0.327 g, 69%). $^1$H NMR: δ 5.06 (t, J=6.7 Hz, 1H, C=CH), 4.24 (broad s, 2H, $POCH_2CH_2N$), 3.89 (broad s, 2H), 3.76 (broad s, 2H), 3.57 (broad s, 2H), 3.40-3.35 (m, 1H, CHO), 3.30 (s, 9H, $N^+qj$ $(CH_3)_3$), 2.40-1.72 (m, 8H), 1.42-1.33 (m, 2H), 1.24 (broad s, 18H, $(CH_2)_9$), 0.84 (t, J=7.0 Hz, 3H, $CH_3$); $^{31}$P NMR: δ −2.16.

Example 2

1-{2-{[(4-Dodecylidenecyclohexyloxy)ethyloxy]hydroxyphosphinyloxy}ethyl}-1-methylpiperidinium inner salt The general procedure described above using 2-(4-dodecylidenecyclohexyloxy)ethanol, TIPS-Cl and N-(2-hydroxyethyl)-N-methylpiperidinium bromide afforded the compound named above (0.350 g, 68%). $^1$H NMR δ: 5.16 (t, J=6.70 Hz, 1H, C=CH), 4.24 (bs, 2H, $POCH_2CH_2N$), 3.82-3.55 (m, 10H), 3.30 (broad s, 1H, CHO), 3.25 (s, 3H, $N^+CH_3$), 1.92-1.43 (m, 14H), 1.41-1.32 (m, 2H, $CH_2CH=$), 1.19 (broad s, 18H, $(CH_2)_9$), 0.83 (t, J=7.0 Hz, 3H, $CH_3$); $^{31}$P NMR δ: −2.1.

Example 3

1-{2-{[(4-Dodecylidenecyclohexyloxy)ethyloxy]hydroxyphosphinyloxy}ethyl}-1-methylmorpholinium inner salt The general procedure described above using 2-(4-dodecylidenecyclohexyloxy)ethanol, TIPS-Cl and N-(2-hydroxyethyl)-N-methylmorpholinium bromide afforded the compound named above (0.330 g, 64%). $^1$H NMR: δ 5.11 (t, J=6.7 Hz, 1H, C=CH), 4.13 (s, 2H, POCH$_2$CH$_2$N), 3.82-3.32 (m, 15H), 3.16 (s, 3H, N$^+$CH$_3$), 1.92-1.47 (m, 8H), 1.42-1.34 (m, 2H, CH$_2$CH=), 1.27 (broad s, 18H, (CH$_2$)$_9$), 0.83 (t, J=7.0 Hz, 3H, CH$_3$); $^{31}$P NMR δ: –2.04.

Example 4

1-{2-{[(4-Tetradecylidenecyclohexyloxy)ethyloxy]hydroxyphosphinyloxy}ethyl}-N,N,N-trimethylammonium inner salt The general procedure described above using 2-(4-tetradecylidenecyclohexyloxy)ethanol, TIPS-Cl and choline chloride afforded the compound named above (0.166 g, 33%). $^1$H NMR: δ 5.05 (t, J=6.7 Hz, 1H, CH=C), 4.23 (broad s, 2H, POCH$_2$CH$_2$N), 3.88 (broad s, 2H), 3.75 (broad s, 2H), 3.55 (broad s, 2H, CH$_2$N), 3.40-3.35 (m, 1H, CHO), 3.32 (s, 9H, N$^+$(CH$_3$)$_3$), 2.41-2.37 (m, 1H), 2.17-2.13 (m, 1H), 1.89-1.74 (m, 8H), 1.21 (broad s, 22H, (CH$_2$)$_{11}$), 0.89 (t, J=7.0 Hz, 3H, CH$_3$); $^{31}$P NMR: δ –2.26; $^{13}$C NMR: δ 136.9, 122.7, 74.3, 67.7, 64.7, 54.2, 33.4, 32.5, 31.9, 30.1, 29.6, 29.3, 27.4, 24.9, 22.6, 14.0.

Example 5

1-{2-{[(4-Tetradecylidenecyclohexyloxy)ethyloxy]hydroxyphosphinyloxy}ethyl}-1-methylpiperidinium inner salt The general procedure described above using 2-(4-tetradecylidenecyclohexyloxy)ethanol, TIPS-Cl and N-(2-hydroxyethyl)-N-methylpiperidinium bromide afforded the compound named above (0.201 g, 37%). $^1$H NMR: δ 5.21 (t, J=6.7 Hz, 1H, CH=C), 4.31 (bs, 2H, POCH$_2$CH$_2$N), 3.93-3.80 (m, 4H), 3.60-3.43 (m, 6H, CH$_2$N(CH$_2$)$_2$), 3.30 (broad s, 4H, NCH$_3$, CHO), 2.40-1.40 (m, 16H), 1.23 (broad s, 22H, (CH$_2$)$_{11}$), 0.88 (t, J=7.0 Hz, 3H, CH$_3$); $^{31}$P NMR: δ –2.4.

Example 6

1-{2-{[(4-Tetradecylidenecyclohexyloxy)ethyloxy]hydroxyphosphinyloxy}ethyl}-1-methylmorpholinium inner salt The general procedure described above using 2-(4-tetradecylidenecyclohexyloxy)ethanol, TIPS-Cl and N-(2-hydroxyethyl)-N-methylmorpholinium bromide afforded the compound named above (0.218 g, 40%). $^1$H NMR: δ 5.06 (t, J=6.7 Hz, 1H, CH=C), 4.07 (broad s, 2H, POCH$_2$CH$_2$N), 3.49-3.17 (m, 5H), 3.11 (s, 3H, N$^+$CH$_3$), 1.99-1.34 (m, 10H), 1.08 (broad s, 22H, (CH$_2$)$_{11}$), 0.78 (t, J=7.0 Hz, 3H, CH$_3$); $^{31}$P NMR: δ –1.9.

Example 7

1-{2-{[(4-Hexadecylidenecyclohexyloxy)ethyloxy]hydroxyphosphinyloxy}ethyl}-N,N,N-trimethylammonium inner salt The general procedure described above using 2-(4-hexadecylidenecyclohexyloxy) ethanol, TIPS-Cl and choline chloride afforded the compound named above (0.196 g, 37%). $^1$H NMR: δ 5.08 (t, J=6.7 Hz, 1H, CH=C), 4.09 (broad s, 2H, OP(O)CH$_2$CH$_2$N), 3.82 (broad s, 2H, OCH$_2$CH$_2$OP), 3.71 (broad s, 2H, OCH$_2$CH$_2$OP), 3.51-3.43 (m, 2H, CH$_2$N), 3.04 (s, 10H, CHO, N$^+$(CH$_3$)$_3$), 2.45-2.40 (m, 1H), 2.25-2.20 (m, 1H), 2.02-1.85 (m, 6H), 1.51-1.42 (m, 2H, CH$_2$CH=), 1.09 (broad s, 26H, (CH$_2$)$_{13}$), 0.71 (t, J=7.0 Hz, 3H, CH$_3$); $^{31}$P NMR: δ –2.04.

Example 8

1-{2-{[(4-Hexadecylidenecyclohexyloxy)ethyloxy]hydroxyphosphinyloxy}ethyl}-1-methylpiperidinium inner salt The general procedure described above using 2-(4-hexadecylidenecyclohexyloxy) ethanol, TIPS-Cl and N-(2-hydroxyethyl)-N-methylpiperidinium bromide afforded the compound named above (0.211 g, 37%). $^1$H NMR: δ 5.13 (t, J=6.7 Hz, 1H, CH=C), 4.35 (broad s, 2H, POCH$_2$), 3.87 (broad s, 2H), 3.78 (broad s, 2H), 3.62-3.45 (m, 6H), 3.26 (broad s, 4H), 2.27-1.63 (m, 8H), 1.52-1.41 (m, 2H, CH$_2$CH=), 1.24 (broad s, 26H, (CH$_2$)$_{13}$), 0.89 (t, J=7.0 Hz, 3H, CH$_3$); $^{31}$P NMR: δ –2.0; $^{13}$C NMR: δ 138.0, 117.4, 75.1, 67.8, 67.7, 64.8, 63.3, 61.8, 58.7, 48.8, 37.2, 31.8, 30.1, 29.7, 29.6, 29.4, 29.3, 28.4, 27.7, 27.2, 22.5, 20.9, 20.1, 14.0.

Example 9

1-{2-{[(4-Hexadecylidenecyclohexyloxy)ethyloxy]hydroxyphosphinyloxy}ethyl}-1-methylmorpholinium inner salt The general procedure described above using 2-(4-hexadecylidenecyclohexyloxy) ethanol, TIPS-Cl and N-(2-hydroxyethyl)-N-methylmorpholinium bromide afforded the compound named above (0.206 g, 36%). $^1$H NMR: δ 5.06 (t, J=6.70 Hz, 1H, CH=C), 4.41 (bs, 2H, POCH$_2$), 3.99-3.39 (m, 15H), 3.35 (s, 3H, N$^+$CH$_3$), 2.45-2.40 (m, 1H, CHCHOCH$_2$), 2.25-2.20 (m, 1H, CH$_2$CHOCH), 2.13-1.85 (m, 6H), 1.22 (broad s, 28H, (CH$_2$)$_{14}$), 0.89 (t, J=7.0 Hz, 3H, CH$_3$); $^{31}$P NMR: δ –2.17; $^{13}$C NMR: δ 136.8, 122.8, 65.3, 60.7, 33.4, 33.3, 32.4, 31.8, 30.1, 29.6, 29.4, 29.3, 27.4, 24.9, 22.6, 14.0.

Example 10

1-{2-[(5-Cyclohexylidenepentyloxy)hydroxyphosphinyloxy]ethyl}-N,N,N-trimethylammonium inner salt The general procedure described above using 5-cyclohexylidenepentanol, MSNT and choline chloride afforded the compound named above (0.219 g, 66%); $^1$H NMR: δ 4.99 (t, J=6.7 Hz, 1H, C=CH), 4.21 (broad s, 2H, POCH$_2$CH$_2$N), 3.74 (broad s, 4H, CH$_2$OPOCH$_2$CH$_2$N), 3.34 (s, 9H, N$^+$(CH$_3$)$_3$), 2.09-1.84 (m, 6H), 1.55-1.28 (m, 10H); $^{31}$P NMR: δ –2.16; $^{13}$C NMR: δ 139.8, 120.8, 66.1, 65.4, 59.1, 54.2, 37.1, 30.6, 28.6, 27.8, 26.9, 26.4, 25.6; ESI-MS m/z: 356.2 (M$^+$+Na$^+$), 334.2 (M$^+$).

Example 11

1-{2-[(5-Cyclohexylidenepentyloxy)hydroxyphosphinyloxy]ethyl}-1-methylpiperidinium inner salt The general procedure described above using 5-cyclohexylidenepentanol, MSNT and N-(2-hydroxyethyl)-N-methylpiperidinium bromide afforded the compound named above (0.153 g, 41%); $^1$H NMR: δ 5.02 (t, J=6.7 Hz, 1H, C=CH), 4.28 (broad s, 2H, POCH$_2$CH$_2$N), 3.82-3.42 (m, 8×, CH$_2$OPOCH$_2$CH$_2$N(CH$_2$)$_2$), 3.31 (s, 3H, N$^+$CH$_3$), 2.08-1.48 (m, 16H), 1.23 (broad s, 6H, (CH$_2$)$_3$); $^{31}$P NMR: δ −2.04; ESI-MS m/z: 374.2 (M$^+$).

Example 12

1-{2-[(5-Cyclohexylidenepentyloxy)hydroxyphosphinyloxy]ethyl}-1-methylmorpholinium inner salt The general procedure described above using 5-cyclohexylidenepentanol, MSNT and N-(2-hydroxyethyl)-N-methylmorpholinium bromide afforded the compound named above (0.153 g, 41%). $^1$H NMR: δ 5.01 (t, J=6.7 Hz, 1H, C=CH), 4.29 (broad s, 2H, POCH$_2$CH$_2$N), 4.11-3.68 (m, 12H), 3.42 (s, 3H, N$^+$CH$_3$), 2.09-1.95 (m, 4H), 1.58-1.49 (m, 6H), 1.31 (broad s, 6H, (CH$_2$)$_3$); $^{31}$P NMR: δ −2.23; ESI-MS m/z: 376.2 (M$^+$).

Example 13

1-{2-[(11-Cyclohexylideneundecyloxy)hydroxyphosphinyloxy]ethyl}-N,N,N-trimethylammonium inner salt The general procedure described above using 11-cyclohexylideneundecanol, MSNT and choline chloride afforded the compound named above (0.220 g, 52%). $^1$H NMR δ: 5.05 (t, J=6.7 Hz, 1H, C=CH), 4.20 (broad s, 2H, POCH$_2$CH$_2$N), 3.75-3.68 (m, 4H, CH$_2$OPOCH$_2$CH$_2$N), 3.26 (s, 9H, N$^+$(CH$_3$)$_3$), 2.11-1.92 (m, 4H), 1.65-1.48 (m, 6H), 1.23 (broad s, 18H, (CH$_2$)$_9$); $^{31}$P NMR: δ −2.45; $^{13}$C NMR: δ 131.0, 124.8, 66.1, 66.0, 59.1, 54.1, 31.0, 30.2, 29.9, 29.7, 29.6, 29.5, 29.3, 28.6, 28.0, 27.8, 27.0, 26.9, 25.9, 25.7; ESI-MS m/z: 440.2 (M$^+$+Na$^+$), 418.2 (M$^+$).

Example 14

1-{2-[(11-Cyclohexylideneundecyloxy)hydroxyphosphinyloxy]ethyl}-1-methylpiperidinium inner salt The general procedure described above using 11-cyclohexylideneundecanol, MSNT and N-(2-hydroxyethyl)-N-methylpiperidinium bromide afforded the compound named above (0.315 g, 69%). $^1$H NMR: δ 4.99 (t, J=6.7 Hz, 1H, C=CH), 4.23 (bs, 2H, POCH$_2$CH$_2$N), 3.78-3.48 (m, 8H, CH$_2$OPOCH$_2$CH$_2$N(CH$_2$)$_2$), 3.27 (s, 3H, N$^+$CH$_3$), 2.04-1.45 (m, 16H), 1.18 (broad s, 18H, (CH$_2$)$_9$); $^{31}$P NMR δ: −2.04; $^{13}$C NMR: δ 130.9, 124.7, 65.3, 63.2, 58.4, 48.5, 37.0, 31.0, 30.9, 30.1, 29.8, 29.6, 29.5, 29.4, 29.2, 28.6, 27.9, 27.7, 26.8, 25.8, 25.6; ESI-MS m/z: 480.3 (M$^+$+Na$^+$), 458.3 (M$^+$).

Example 15

1-{2-[(11-Cyclohexylideneundecyloxy)hydroxyphosphinyloxy]ethyl}-1-methylmorpholinium inner salt The general procedure described above using 11-cyclohexylideneundecanol, MSNT and N-(2-hydroxyethyl)-N-methylmorpholinium bromide afforded the compound named above (0.117 g, 25%). $^1$H NMR: δ 5.05 (t, J=6.7 Hz, 1H, C=CH), 4.29 (broad s, 2H, POCH$_2$CH$_2$N), 3.99-3.70 (m, 12H), 3.48 (s, 3H, N$^+$CH$_3$), 2.08-1.92 (m, 4H), 1.65-1.48 (m, 6H), 1.23 (s, 18H, (CH$_2$)$_9$); $^{31}$P NMR: δ −2.13; $^{13}$C NMR: δ 131.0, 124.8, 65.8, 64.3, 60.7, 58.5, 48.3, 37.1, 31.0, 30.9, 29.9, 29.7, 29.6, 29.5, 29.4, 29.3, 28.6, 28.2, 28.0, 27.8, 27.0, 25.8, 25.7, 17.6.

Example 16

1-{2-[(5-Adamantylidenepentyloxy)hydroxyphosphinyloxy]ethyl}-N,N,N-trimethylammonium inner salt The general procedure described above using 5-adamantylidenepentanol, MSNT and choline chloride afforded the compound named above (0.223 g, 58%). $^1$H NMR: δ 4.96 (t, J=6.7 Hz, 1H, C=CH), 4.22 (broad s, 2H, POCH$_2$CH$_2$N), 3.77-3.71 (m, 4H, CH$_2$OPOCH$_2$CH$_2$N), 3.29 (s, 9H, N$^+$(CH$_3$)$_3$), 2.75 (s, 1H, CHC=), 2.27 (s, 1H, CHC=), 1.95-1.53 (m, 16l), 1.34-1.29 (m, 2H); $^{31}$P NMR: δ −2.42; $^{13}$C NMR: δ 147.7, 115.9, 66.3, 65.5, 59.1, 54.3, 40.5, 39.8, 38.9, 37.2, 32.0, 30.6, 28.6, 26.6, 26.2; ESI-MS m/z: 408.1 (M$^+$+Na$^+$), 386.1 (M$^+$).

Example 17

1-{2-[(5-Adamantylidenepentyloxy)hydroxyphosphinyloxy]ethyl}-1-methylpiperidinium inner salt The general procedure described above using 5-adamantylidenepentanol, MSNT and N-(2-hydroxyethyl)-N-methylpiperidinium bromide afforded the compound named above (0.272 g, 64%). $^1$H NMR δ: 4.93 (t, J=6.7 Hz, 1H, C=CH), 4.25 (broad s, 2H, POCH$_2$CH$_2$N), 3.79-3.60 (m, 8H, CH$_2$OPOCH$_2$CH$_2$N(CH$_2$)$_2$), 3.32 (s, 3H, N$^+$(CH$_3$)$_3$), 2.72 (s, 1H, CHC=), 2.24 (s, 1H, CHC=), 1.92-1.50 (m, 22H), 1.31-1.26 (m, 2H); $^{31}$P NMR: δ −1.9; $^{13}$C NMR: δ 147.6, 115.9, 65.4, 65.3, 63.5, 58.6, 58.5, 48.6, 40.5, 39.8, 38.9, 37.2, 32.0, 30.7, 30.6, 28.6, 26.6, 26.2, 20.9, 20.2; ESI-MS m/z: 448.2 (M$^+$+Na$^+$), 426.2 (M$^+$).

Example 18

1-{2-[(5-Adamantylidenepentyloxy)hydroxyphosphinyloxy]ethyl}-1-methylmorpholinium inner salt The general procedure described above using 5-adamantylidenepentanol, MSNT and N-(2-hydroxyethyl)-N-methylmorpholinium bromide afforded the compound named above (0.239 g, 56%). $^1$H NMR δ: 4.94 (t, J=6.7 Hz, 1H, C=CH), 4.27 (broad s, 2H, POCH$_2$CH$_2$N), 3.99-3.69 (m, 12H), 3.43 (s, 3H, N$^+$CH$_3$), 2.73 (s, 1H, CHC=), 2.25 (s, 1H, CHC=), 1.96-1.32 (m, 16H), 1.29-1.18 (m, 2H); $^{31}$P NMR: δ −2.16; $^{13}$C NMR: δ 147.8, 115.8, 65.6, 65.5, 64.3, 60.7, 58.5, 48.3, 40.5, 39.8, 38.9, 37.2, 32.0, 30.6, 30.5, 28.6, 26.6, 26.5; ESI-MS m/z: 450.2 (M$^+$+Na$^+$), 428.2 (M$^+$).

Example 19

1-{2-[(11-Adamantylideneundecyloxy)hydroxyphosphinyloxy]ethyl}-N,N,N-trimethylammonium inner salt The general procedure described above using 11-adamantylideneundecanol, MSNT and choline chloride afforded the compound named above (0.248 g, 53%). $^1$H NMR: δ 4.98 (t, J=6.7 Hz, 1H, C=CH), 4.21 (broad s, 2H, POCH$_2$CH$_2$N), 3.75 (broad s, 4H, CH$_2$OPOCH$_2$CH$_2$N), 3.32 (s, 9H, N$^+$(CH$_3$)$_3$), 2.77 (s, 1H, CHC=), 2.28 (s, 1H, CHC=), 1.91-1.53 (m, 16H), 1.23 (broad s, 14H); $^{31}$P NMR: δ −2.16; $^{13}$C NMR: δ: 147.2, 116.3, 66.1, 65.5, 59.2, 54.2, 40.5, 39.8, 38.9, 37.3, 32.0, 31.0, 30.9, 29.7, 29.6, 29.5, 29.2, 28.7, 26.5, 25.9; ESI-MS m/z: 492.2 (M$^+$+Na$^+$), 470.2 (M$^+$).

Example 20

1-{2-[(11-Adamantylideneundecyloxy)hydroxyphosphinyloxy]ethyl}-1-methylpiperidinium inner salt The general procedure described above using 11-adamantylideneundecanol, MSNT and N-(2-hydroxyethyl)-N-methylpiperidinium bromide afforded the compound named above (0.168 g, 33%). $^1$H NMR δ: 4.98 (t, J=6.7 Hz, 1H, C=CH), 4.27 (broad s, 2H, POCH$_2$CH$_2$N), 3.84-3.52 (m, 8H, CH$_2$OPOCH$_2$CH$_2$N(CH$_2$)$_2$), 3.32 (s, 3H, NCH$_3$), 2.76 (s, 1H, CHC=), 2.27 (s, 1H, CHC=), 1.92-1.53 (m, 22H), 1.23 (broad s, 14H); $^{31}$P NMR: δ –2.04; $^{13}$C NMR: δ 147.2, 116.3, 65.1, 62.1, 57.3, 47.4, 40.5, 39.9, 38.9, 37.5, 32.0, 30.3, 29.6, 29.5, 29.4, 29.2, 28.7, 26.4, 25.8, 20.9, 20.2; ESI-MS m/z: 532.3 (M$^+$+Na$^+$), 510.3 (M$^+$).

Example 21

1-{2-[(11-Adamantylideneundecyloxy)hydroxyphosphinyloxy]ethyl}-1-methylmorpholinium inner salt The general procedure described above using 11-adamantylideneundecanol, MSNT and N-(2-hydroxyethyl)-N-methylmorpholinium bromide afforded the compound named above (0.235 mg, 46%). $^1$H NMR: δ 4.99 (t, J=6.7 Hz, 1H, C=CH), 4.29 (broad s, 2H, POCH$_2$CH$_2$N), 4.00-3.67 (m, 12H), 3.42 (s, 3H, N$^+$CH$_3$), 2.77 (s, 1H, CHC=), 2.28 (s, 1H, CHC=), 1.91-1.54 (m, 14H), 1.23 (s, 16H); $^{31}$P NMR: δ –2.29; $^{13}$C NMR: δ 147.2, 116.3, 65.7, 64.9, 60.7, 58.5, 48.3, 40.5, 39.8, 38.9, 37.3, 32.0, 30.9, 30.4, 29.7, 29.6, 29.5, 29.3, 28.6, 26.5, 25.8; ESI-MS m/z: 534.2 (M$^+$+Na$^+$), 512.2 (M$^+$).

Example 22

1-{2-{[(4-(Dodecyloxy)cyclohexyloxy)ethyloxy]hydroxyphosphinyloxy}ethyl}-1-methylpiperidinium inner salt The general procedure described above using 2-[4-(dodecyloxy)cyclohexyloxy]ethanol, TIPS-Cl and N-(2-hydroxyethyl)-N-methylpiperidinium bromide afforded the compound named above (0.241 g, 45%). $^1$H NMR: δ 4.26 (bs, 2H), 3.88-3.79 (m, 4H), 3.58-3.38 (m, 6H), 3.36-3.27 (m, 7H), 1.95-1.40 (m, 34H), 0.83 (t, J=7.0 Hz, 3H); $^{31}$P NMR: δ –2.26.

Example 23

1-{2-{[(4-(Dodecyloxy)cyclohexyloxy)ethyloxy]hydroxyphosphinyloxy}ethyl}-1-methylmorpholinium inner salt The general procedure described above using 2-[4-(dodecyloxy)cyclohexyloxy]ethanol, TIPS-Cl and N-(2-hydroxyethyl)-N-methylmorpholinium bromide afforded the compound named above (0.213 g, 40%). $^1$H NMR: δ 4.32 (broad s, 2H), 4.04-3.19 (m, 21H), 1.99-1.50 (m, 28H), 0.86 (t, J=7.0 Hz, 3H, CH$_3$); $^{31}$P NMR: δ –2.5.

Example 24

1-{2-{[(4-(Tetradecyloxy)cyclohexyloxy)ethyloxy]hydroxyphosphinyloxy}ethyl}-1-methylpiperidinium inner salt The general procedure described above using 2-[4-(tetradecyloxy)cyclohexyloxy]ethanol, TIPS-Cl and choline chloride afforded the compound named above (0.214 g, 38%).
$^1$H NMR: δ 4.31 (bs, 2H), 3.93-3.84 (m, 4H), 3.62-3.54 (m, 6H), 3.36-3.27 (m, 7H), 1.87-1.20 (m, 38H), 0.83 (t, J=7.0 Hz, 3H); $^{31}$P NMR: δ –2.32.

Example 25

1-{2-{[(4-(Tetradecyloxy)cyclohexyloxy)ethyloxy]hydroxyphosphinyloxy}ethyl}-1-methylmorpholinium inner salt The general procedure described above using 2-[4-(tetradecyloxy)cyclohexyloxy]ethanol, TIPS-Cl and N-(2-hydroxyethyl)-N-methylmorpholinium bromide afforded the compound named above (0.236 g, 42%). $^1$H NMR: δ 4.32 (broad s, 2H), 3.96-3.19 (m, 21H), 1.89-1.50 (m, 32H), 0.86 (t, J=7.0 Hz, 31); $^{31}$P NMR: δ –2.11.

General Procedure for the Hydrogenation of the Unsaturated Ether Phospholipids

To a solution of the desired ether phospholipid (1 mmol) in MEOH (10 mL) was added 10% Pd/C (10% w/w) and the resulting mixture was hydrogenated at 1 Atm for 10 h. Filtration through celite and evaporation of the filtrate in vacuo afforded the pure product.

Example 26

1-{2-{[(4-Dodecylcyclohexyloxy)ethyloxy]hydroxyphosphinyloxy}ethyl}-N,N,N-trimethylammonium inner salt The general procedure described above using the compound of Example 1 afforded the compound named above (yield quantitative). $^1$H NMR: δ: 4.31 (broad s, 2H, POCH$_2$CH$_2$N), 3.93 (broad s, 2H, CH$_2$OPOCH$_2$CH$_2$N), 3.82 (broad s, 2H), 3.59 (broad s, 2H, POCH$_2$CH$_2$N), 3.37 (broad s, 10H, CHO, N$^+$(CH$_3$)$_3$), 2.05-1.95 (m, 1H), 1.76-1.72 (m, 2H), 1.46-1.10 (m, 28H), 0.86 (t, J=7.0 Hz, 3H, CH$_3$).

Example 27

1-{2-{[(4-Tetradecylcyclohexyloxy)ethyloxy]hydroxyphosphinyloxy}ethyl}-N,N,N-trimethylammonium inner salt The general procedure described above using the compound of Example 4 afforded the compound named above (yield quantitative). $^1$H NMR: δ 4.31 (broad s, 2H, POCH$_2$CH$_2$N), 3.93-3.82 (m, 4H), 3.59-3.15 (m, 12H), 1.96 (broad s, 1H), 1.76 (broad s, 2H), 1.42-1.09 (m, 32H), 0.87 (t, J=7.0 Hz, 3H, CH$_3$).

Example 28

1-{2-[(11-Cyclohexylundecyloxy)hydroxyphosphinyloxy]ethyl}-N,N,N-trimethylammonium inner salt The general procedure described above using the compound of Example 13 afforded the compound named above (yield quantitative). $^1$H NMR: δ 4.20 (broad s, 2H, POCH$_2$CH$_2$N), 3.75-3.68 (m, 4H, CH$_2$OPOCH$_2$CH$_2$N), 3.26 (s, 9H, N$^+$(CH$_3$)$_3$), 2.09-1.12 (m, 13H), 1.23 (s, 18H, (CH$_2$)$_9$).

Example 29

1-{2-[(5-Adamantylpentyloxy)hydroxyphosphinyloxy]ethyl}-N,N,N-trimethylammonium inner salt The general procedure described above using the compound of Example 16 afforded the compound named above (yield quantitative). $^1$H NMR: δ 4.27 (bs, 2H, POCH$_2$CH$_2$N), 3.79-3.09 (m, 13H), 2.02-1.25 (m, 23H).

Example 30

1-{2-[(11-Adamantylundecyloxy)hydroxyphosphinyloxy]ethyl}-N,N,N-trimethylammonium inner salt The general procedure described above using the compound of Example 19 afforded the compound named above (yield quantitative). $^1$H NMR: δ 4.27 (broad s, 2H, POCH$_2$CH$_2$N), 3.79-3.09 (m, 13H), 2.02-1.25 (m, 35H).

Determination of in Vitro Antileishmanial Activity in Promastigote Cultures.

The effect of the phospholipids according to the present invention against the promastigote forms of *Leishmania donovani* and *Leishmania infantum* was evaluated using an MTT (3-(4,5-dimethylthiazol-2yl)-2,5-diphenyltetrazolium bromide)-based enzymatic method as a marker of cell viability and was compared with that of the ether phospholipid hexadecylphosphocholine (Miltefosine). Thus, promastigotes of *Leishmania infantum* MHOM/TN/80/IPT1/LEM 235 and *Leishmania donovani* MHOM/IN/80/DD8/LEM 703, were grown in RPMI 1640 supplemented with 10% FCS, *L. glutamine* and antibiotics, at 26° C. All new compounds were dissolved in DMSO to a final concentration of 9.625 mM and linear 3-fold dilutions were done in the culture medium. 25 μL of promastigote culture at 5×10$^5$ cells/mL were cultured in a 96-well flat-bottom plate (Costar 3696), and incubated with 25 μL of different drug concentrations at 26° C. After 72 h, 10 μL of 5 mg/mL MTT in PBS (SIGMA M2128) were added and incubation was continued for 3 h. The reaction was stopped by the addition of 50 μL of 50% isopropanol, 10% SDS under gentle shacking for 30 min. Absorbance was measured at 550 nm with reference at 620 nm in a TRITURUS microplate reader.

TABLE 1

In vitro antileishmanial activity* against the promastigote forms of *L. infantum* and *L. donovani* of phospholipids of the present invention.

| Compound | IC$_{50}$ (μM) L. infantum MON 235 | IC$_{50}$ (μM) L. donovani MON 703 |
|---|---|---|
| Miltefosine | 22.56 ± 3.6 | 23.71 ± 4.07 |
| 1-{2-{[(4-Dodecylidenecyclohexyloxy)ethyloxy]hydroxyphosphinyloxy}ethyl}-N,N,N-trimethylammonium inner salt. | 3.25 ± 0.65 | 7.08 ± 1.2 |
| 1-{2-{[(4-Dodecylidenecyclohexyloxy)ethyloxy]hydroxyphosphinyloxy}ethyl}-1-methylpiperidinium inner salt. | 23.07 ± 3.6 | 22 ± 3.25 |
| 1-{2-{[(4-Dodecylidenecyclohexyloxy)ethyloxy]hydroxyphosphinyloxy}ethyl}-1-methylmorpholinium inner salt. | 16.46 ± 1.8 | 50.67 ± 3.6 |
| 1-{2-{[(4-Tetradecylidenecyclohexyloxy)ethyloxy]hydroxyphosphinyloxy}ethyl}-N,N,N-trimethylammonium inner salt. | 5.25 ± 0.45 | 3.91 ± 0.21 |
| 1-{2-{[(4-Tetradecylidenecyclohexyloxy)ethyloxy]hydroxyphosphinyloxy)ethyl}-1-methylpiperidinium inner salt. | 11.4 ± 2.4 | 29.7 ± 3.6 |
| 1-{2-{[(4-Tetradecylidenecyclohexyloxy)ethyloxy]hydroxyphosphinyloxy)ethyl}-1-methylmorpholinium inner salt. | 15.5 ± 1.8 | 38.6 ± 3.2 |
| 1-{2-{[(4-Hexadecylidenecyclohexyloxy)ethyloxy]hydroxylphosphinyloxy)ethyl}-N,N,N-trimethylammonium inner salt. | 21.19 ± 2.6 | 45.1 ± 7.2 |
| 1-{2-{[(4-Hexadecylidenecyclohexyloxy)ethyloxy]hydroxyphosphinyloxy}ethyl}-1-methylpiperidinium inner salt. | 6.5 ± 1.7 | 21.96 ± 1.99 |
| 1-{2-{[(4-Hexadecylidenecyclohexyloxy)ethyloxy]hydroxyphosphinyloxy}ethyl}-1-methylmorpholinium inner salt. | 3.7 ± 0.71 | 16.22 ± 2.29 |
| 1-{2-[(5-Cyclohexylidenepentyloxy)hydroxyphosphinyloxy]ethyl}-N,N,N-trimethylammonium inner salt. | >100 | >100 |
| 1-{2-[(5-Cyclohexylidenepentyloxy)hydroxyphosphinyloxy]ethyl}-1-methylpiperidinium inner salt. | >100 | >100 |
| 1-{2-[(5-Cyclohexylidenepentyloxy)hydroxyphosphinyloxy]ethyl}-1-methylmorpholinium inner salt. | >100 | >100 |
| 1-{2-[(11-Cyclohexylideneundecyloxy)hydroxyphosphinyloxy]ethyl}-N,N,N-trimethylammonium inner salt. | 5.2 ± 1.5 | 2.4 ± 0.6 |
| 1-{2-[(11-Cyclohexylideneundecyloxy)hydroxyphosphinyloxy]ethyl}-1-methylpiperidinium inner salt. | 47.6 ± 7.33 | 8.7 ± 1 |
| 1-{2-[(11-Cyclohexylideneundecyloxy)hydroxyphosphinyloxy]ethyl}-1-methylmorpholinium inner salt. | 22.8 ± 1.7 | 8.25 ± 0.25 |
| 1-{2-[(5-Adamantylidenepentyloxy)hydroxyphosphinyloxy]ethyl}-N,N,N-trimethylammonium inner salt. | >100 | 4.99 ± 1.50 |
| 1-{2-[(5-Adamantylidenepentyloxy)hydroxyphosphinyloxy]ethyl}-1-methylpiperidinium inner salt. | >100 | >100 |
| 1-{2-[(5-Adamantylidenepentyloxy)hydroxyphosphinyloxy]ethyl}-1-methylmorpholinium inner salt. | >100 | 46.85 ± 8.7 |
| 1-{2-[(11-Adamantylideneundecyloxy)hydroxyphosphinyloxy]ethyl}-N,N,N-trimethylammonium inner salt. | 6.75 ± 2.4 | 3.16 ± 0.63 |
| 1-{2-[(11-Adamantylideneundecyloxy)hydroxyphosphinyloxy]ethyl}-1-methylpiperidinium inner salt. | 22.58 ± 3.4 | 5.41 ± 1.14 |
| 1-{2-[(11-Adamantylideneundecyloxy)hydroxyphosphinyloxy]ethyl}-1-methylmorpholinium inner salt. | 6.64 ± 1.2 | 5.09 ± 1.86 |

TABLE 1-continued

In vitro antileishmanial activity* against the promastigote forms of L. infantum and L. donovani of phospholipids of the present invention.

| Compound | $IC_{50}$ (µM) L. infantum MON 235 | $IC_{50}$ (µM) L. donovani MON 703 |
|---|---|---|
| 1-{2-{[(4-Dodecylcyclohexyloxy)ethyloxy]hydroxy-phosphinyloxy}ethyl-N,N,N-trimethylammonium inner salt. | 5.65 ± 1.93 | 9.49 ± 1.4 |
| 1-{2-{[(4-Tetradecylcyclohexyloxy)ethyloxy]hydroxy-phosphinyloxy}ethyl}-N,N,N-trimethylammonium inner salt. | 23.3 ± 3.5 | 23.65 ± 4.4 |
| 1-{2-[(11-Cyclohexylundecyloxy)hydroxyphosphinyloxy]ethyl}-N,N,N-trimethylammonium inner salt. | 8.4 ± 0.8 | 10.3 ± 1.3 |
| 1-{2-[(5-Adamantylpentyloxy)hydroxyphosphinyloxy]ethyl}-N,N,N-trimethylammonium inner salt. | >100 | 4.02 ± 2.3 |
| 1-{2-[(11-Adamantylundecyloxy)hydroxyphosphinyloxy]ethyl}-N,N,N-trimethylammonium inner salt. | 5.97 ± 1.06 | 2.88 ± 0.72 |

*Results are expressed as mean ± SEM, n = 3-4 (each run in duplicate).

It is worth noting that the length of the alkyl chain of active compounds of the present invention varies from 5 to 11 carbon atoms for the alkylphosphocholine analogues and from 12 to 14 for the alkoxyethylphosphocholine analogues. This could be advantageous for the solubility and/or the toxicity of the new compounds and also for their metabolic clearance. Thus, we proceeded to assess the cytotoxicity of four inventive compounds as well as miltefosine in the human monocytic cell line THP1.

Assessment of Cytotoxicity in THP1 Monocyte Cells.

As a quantitative measurement of the cell damage after incubation with different concentrations of drugs dual staining with SYBR-14 and PI (Molecular Probes, The Netherlands) was used followed by flow cytometry.

Staining with PI and SYBR-14

THP1 cell cultures were incubated at $1\times10^6$ cells/ml with different concentrations of the compounds ranging from 50 to 1.56 µM. After an incubation period of 72 hours approximately $4\times10^6$ cells were suspended in labeling buffer (10 mM HEPES, 150 mM NaCl, 10% BSA, pH 7.4) and 10 µg/ml PI and 0.1 mg/ml SYBR-14 were added. The cultures were incubated at 37° C. for 30 minutes before analysis by flow cytometry.

Flow Cytometry Analysis.

Cell samples were analyzed on an Epics Elite model flow cytometer (Coulter, Miami, Fla.). The green fluorescence of SYBR-14 and the red fluorescence of PI were excited at 488 nm. At least 10,000 cells were analyzed per sample and each staining experiment was repeated twice. Data analysis was performed on fluorescence intensities that excluded cell autofluorescence and cell debris.

THP1 monocytes infected with the appropriate *Leishmania* species were used for the evaluation of the leishmanicidal activity of the compounds against the intracellular amastigote stages of the parasite. As shown in FIG. 1, the evaluation of cytotoxic activity on infected THP1 monocytes with *L. donovani* and *L. infantum* showed a very strong cytotoxic effect of miltefosine on THP1 cells at concentrations as low as 50 µM, which was not observed with two of the most active analogues (compounds 13 and 19) of the present invention.

We claim:
1. A compound, represented by the general formula

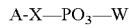

or a physiologically acceptable salt, or an isomer or stereoisomer, wherein:

A is a radical selected from one of the formulae Y, $YR^1$, $R^1Y$, $R^1YR^4$, $R^1OY$, $YOR^1$, $R^1YOR^2$ or $R^1OYOR^2$;

W is a radical of the formulae $R^3Q$ or a C4 to C7 non-aromatic heterocycle containing a nitrogen heteroatom wherein said heterocycle consists of at least one heteroatom independently selected from nitrogen, oxygen, sulfur and combinations thereof, and wherein said heterocycle can be substituted with one or more substituent groups;

Y is a carbocyclic ring, a carbocyclic ring consisting of at least one substituent group, a fused bicyclic ring system, a fused bicyclic ring system consisting of at least one substituent group, a bridged bicyclic ring system, a bridged bicyclic ring system consisting of at least one substituent group, a bridged tricyclic ring system, a bridged tricyclic ring system consisting of at least one substituent group;

X is a valency bond, a methylene group (—$CH_2$—) or a heteroatom selected from nitrogen, oxygen, sulfur;

$R^1$ is a C5 to C18 alkylidene group or C5 to C18 alkyl group, any possible member selected from a substituted or unsubstituted carbocyclic ring having about 3 to about 7 ring members, a C3 to C20 saturated, straight or branched, aliphatic hydrocarbon chain, a C3 to C20 unsaturated straight or branched, aliphatic hydrocarbon chain having 4 or fewer double bonds, a C3 to C20 saturated or unsaturated, straight or branched, aliphatic hydrocarbon chain consisting of one or more independently chosen heteroatoms, a C3 to C20 saturated or unsaturated, straight or branched, aliphatic hydrocarbon chain consisting of at least one independently chosen possible member selected from a carbocyclic ring having about 4 to about 7 ring members, or any above member consisting of a substituent group on at least one available ring atom, or any above C3 to C20 hydrocarbon chain having at least one independently chosen substituent group;

$R^2$ is any possible member selected from a substituted or unsubstituted carbocyclic ring having about 3 to about 7 ring members, an about C2 to about C5 saturated, straight or branched, aliphatic hydrocarbon chain, an about C3 to about C20 unsaturated straight or branched, aliphatic hydrocarbon chain with 4 or fewer double bonds, an about C2 to about C5 saturated or unsaturated, straight or branched, aliphatic hydrocarbon chain consisting of one or more independently chosen heteroatoms, an about C2 to about C5 saturated or unsaturated, straight or branched, aliphatic hydrocarbon chain consisting of at least one independently chosen possible member selected from a carbocyclic ring having about 4 to about 7 ring members, or any above member consisting of a substituent group on at least one available ring atom, or any above about C2 to about C5 hydrocarbon chain having at least one independently chosen substituent group;

$R^3$ is any possible member selected from a carbocyclic ring having about 3 to about 9 ring members, a heterocyclic ring having about 4 to about 9 ring members, an aromatic ring having about 5 to about 9 ring members, a heteroaromatic ring having about 5 to about 9 ring members; any above group consisting of a substituent group on at least one available ring atom, an about C2 to about C5 saturated or unsaturated, straight or branched, aliphatic hydrocarbon chain, an about C2 to about C5 saturated or unsaturated, straight or branched, aliphatic hydrocarbon chain consisting of one or more independently chosen heteroatoms, an about C2 to about C5 saturated or unsaturated, straight or branched, aliphatic hydrocarbon chain consisting of at least one independently chosen possible member selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; or any above member consisting of a substituent group on at least one available ring atom, or any above about C2 to about C5 hydrocarbon chain having at least one independently chosen substituent group;

$R^4$ is any group independently selected from $R^1$ or $R^2$; and

Q is an ammonium group, wherein said ammonium group can be substituted one or more times with a C1 to C6 alkyl radical, or is a C3 to C7 heterocycle containing a nitrogen heteroatom which is bonded to the $R^3$ group, wherein said heterocycle can contain one or more heteroatoms independently selected from nitrogen, oxygen, sulfur and combinations thereof, and wherein said heterocycle can be substituted with one or more substituent groups, a heterobicyclic ring containing a nitrogen heteroatom which is bonded to the $R^3$ group, wherein said heterobicyclic ring can contain one or more heteroatoms independently selected from nitrogen, oxygen, sulfur and combinations thereof, and wherein said heterobicyclic ring can be substituted with one or more substituent groups, a heterotricyclic ring containing a nitrogen heteroatom which is bonded to the $R^3$ group, wherein said heterotricyclic ring can contain one or more heteroatoms independently selected from nitrogen, oxygen, sulfur and combinations thereof, and wherein said heterotricyclic ring can be substituted with one or more substituent groups; advantageously the substituent groups are independently selected from hydroxyl, halogen, alkyl, cycloalkyl, aryl, alkoxy, alkoxycarbonyl, alkylthio or amino.

2. The compound of claim 1, wherein A is $YR^1$, $R^1YOR^2$ or $R^1OYOR^2$.

3. The compound of claim 1, wherein the W is a C4 to C7 non-aromatic heterocycle containing a nitrogen heteroatom wherein said heterocycle consisting of at least one heteroatom independently selected from nitrogen, oxygen, sulfur and combinations thereof, and wherein said heterocycle can be substituted with one or more substituent groups independently selected from hydroxyl, halogen, alkyl, cycloalkyl, aryl, alkoxy, alkoxycarbonyl, alkylthio or amino.

4. The compound of claim 1, wherein X is an oxygen atom.

5. The compound of claim 1, wherein $R^1$ is a C3 to C20 saturated or unsaturated, straight or branched, aliphatic hydrocarbon chain consisting of a substituent group on at least one available ring atom, wherein the substituent groups are independently selected from hydroxyl, halogen, alkyl, cycloalkyl, aryl, alkoxy, alkoxycarbonyl, alkylthio or amino, or a C3 to C20 unsaturated straight or branched, aliphatic hydrocarbon chain with not more than 4 double bonds, comprising a substituent group on at least one available ring atom, wherein the substituent groups are independently selected from hydroxyl, halogen, alkyl, cycloalkyl, aryl, alkoxy, alkoxycarbonyl, alkylthio or amino.

6. The compound of claim 1, wherein $R^2$ is a C2 saturated or unsaturated alkyl or alkenyl, a C2 saturated or unsaturated alkyl or alkenyl which can be substituted with one or more substituents selected from hydroxyl, halogen, alkyl, cycloalkyl, aryl, alkoxy, alkoxycarbonyl, alkylthio and amino.

7. The compound of claim 1, wherein $R^3$ is a C2 saturated or unsaturated alkyl or alkenyl, a C2 saturated or unsaturated alkyl or alkenyl which can be substituted with one or more substituents selected from hydroxyl, halogen, alkyl, cycloalkyl, aryl, arylalkyl, alkoxy, alkoxycarbonyl, alkylthio and amino or a C3 to C8 cycloalkyl which is bonded at C1 to the oxygen and at C2 to Q.

8. The compound of claim 1, wherein Q is a C3 to C7 heterocycle containing a nitrogen heteroatom which is bonded to the $R^3$ group, wherein said heterocycle can contain one or more heteroatoms independently selected from nitrogen, oxygen, sulfur and combinations thereof, and wherein said heterocycle can be substituted with one or more substituent groups, independently selected from hydroxyl, halogen, alkyl, cycloalkyl, aryl, alkoxy, alkoxycarbonyl, alkylthio or amino.

9. The compound of claim 1, wherein $R^1$ is a C5 to C18 alkylidene group or C5 to C18 alkyl group.

10. The compound of claim 1, wherein $R^1$ is pentylidene, undecylidene, dodecylidene, tetradecylidene, hexadecylidene, pentyl, undecyl, dodecyl, tetradecyl or hexadecyl groups.

11. The compound of claim 1, wherein Y is a C3 to C6 carbocyclic ring, a substituted carbocyclic ring, a bridged tricyclic ring system, or a substituted bridged tricyclic ring system.

12. The compound of claim 1, wherein Y is cyclohexyl, or adamantyl.

13. The compound of claim 1, wherein $R^2$ is a C2 saturated alkyl.

14. The compound of claim 1, wherein Q is trimethylammonium, N-methylmorpholinio or N-methylpiperidinio.

15. The compound of claim 1, wherein:

A is $R^1YOR^2$;

W is $R^3Q$;

X is oxygen;

Y residue is a carbocyclic ring, a substituted carbocyclic ring, a bridged tricyclic ring system, or a substituted bridged tricyclic ring system;

$R^1$ is a C12 to C18 alkylidene group or C12 to C18 alkyl group;

$R^2$ is a C2 saturated alkyl;

$R^3$ is a C2 saturated alkyl; and

Q is an ammonium group, wherein said ammonium group can be substituted one or more times with a C1 to C6 alkyl radical, or is a C3 to C7 heterocycle containing a nitrogen heteroatom which is bonded to the $R^3$ group, wherein said heterocycle can contain one or more heteroatoms selected from nitrogen, oxygen or sulfur, and wherein said heterocycle can be substituted with one or more independently chosen substituents.

16. The compound of claim 1, which is one or more of 1-{2-{[(4-Dodecylidenecyclohexyloxy)ethyloxy]hydroxyphosphinyloxy}ethyl}-N,N,N-trimethylammonium inner salt; 1-{2-{[(4-Dodecylidenecyclohexyloxy)ethyloxy]hydroxyphosphinyloxy}ethyl}-1-methylpiperidinium inner salt; 1-{2-{[(4-Dodecylidenecyclohexyloxy)ethyloxy]hydroxyphosphinyloxy}ethyl}-1-methylmorpholinium inner salt; 1-{2-{[(4-Tetradecylidenecyclohexyloxy)ethyloxy]hydroxyphosphinyloxy}ethyl}-N,N,N-trimethylammonium inner salt; 1-{2-{[(4-Tetradecylidenecyclohexyloxy)ethyloxy]hydroxyphosphinyloxy}ethyl}-1-ethylpiperidinium inner salt; 1-{2-{[(4-Tetradecylidenecyclohexyloxy)ethyloxy]hydroxyphosphinyloxy}ethyl}-1-methylmorpholinium inner salt; 1-{2-{[(4-Hexadecylidenecyclohexyloxy)ethyloxy]hydroxyphosphinyloxy}ethyl}-N,N,N-trimethylammonium inner salt; 1-{2-{[(4-Hexadecylidenecyclohexyloxy)ethyloxy]hydroxyphosphinyloxy}ethyl}-1-methylpiperidinium inner salt; 1-{2-{[(4-Hexadecylidenecyclohexyloxy)ethyloxy]hydroxyphosphinyloxy}ethyl}-1-methylmorpholinium inner salt; 1-{2-{[(4-Dodecylcyclohexyloxy)ethyloxy]hydroxyphosphinyloxy}ethyl-N,N,N-trimethylammonium inner salt; or 1-{2-{[(4-Tetradecylcyclohexyloxy)ethyloxy]hydroxyphosphinyloxy}ethyl}-N,N,N-trimethylammonium inner salt.

17. The compound of claim 1 wherein
A is YR$^1$;
W is R$^3$Q;
X is oxygen;
Y residue is a carbocyclic ring, a substituted carbocyclic ring, a bridged tricyclic ring system, a substituted bridged tricyclic ring system or an aromatic system;
R$^1$ is a C5 to C18 alkylidene group or C5 to C18 alkyl group;
R$^3$ is a C2 saturated alkyl; and
Q is an ammonium group, wherein said ammonium group can be independently substituted one or more times with a C1 to C6 alkyl radical, or is a C3 to C7 heterocycle containing a nitrogen heteroatom which is bonded to the R$^3$ group, wherein said heterocycle can contain one or more heteroatoms independently selected from nitrogen, oxygen or sulfur, and wherein said heterocycle can be substituted with one or more independently chosen substituents.

18. A compound of claim 16, selected from 1-{2-[(5-Cyclohexylidenepentyloxy)hydroxyphosphinyloxy]ethyl}-N,N,N-trimethylammonium inner salt; 1-{2-[(5-Cyclohexylidenepentyloxy)hydroxyphosphinyloxy]ethyl}-1-methylpiperidinium inner salt; 1-{2-[(5-Cyclohexylidenepentyloxy)hydroxyphosphinyloxy]ethyl}-1-methylmorpholinium inner salt; 1-{2-[(11-Cyclohexylideneundecyloxy)hydroxyphosphinyloxy]ethyl}-N,N,N-trimethylammonium inner salt; 1-{2-[(11-Cyclohexylideneundecyloxy)hydroxyphosphinyloxy]ethyl}-1-methylpiperidinium inner salt; 1-{2-[(11-Cyclohexylideneundecyloxy)hydroxyphosphinyloxy]ethyl}-1-methylmorpholinium inner salt; 1-{2-[(5-Adamantylidenepentyloxy)hydroxyphosphinyloxy]ethyl}-N,N,N-trimethylammonium inner salt; 1-{2-[(5-Adamantylidenepentyloxy)hydroxyphosphinyloxy]ethyl}-1-methylpiperidinium inner salt; 1-{2-[(5-Adamantylidenepentyloxy)hydroxyphosphinyloxy]ethyl}-1-methylmorpholinium inner salt; 1-{2-[(11-Adamantylideneundecyloxy)hydroxyphosphinyloxy]ethyl}-N,N,N-trimethylammonium inner salt; 1-{2-[(11-Adamantylideneundecyloxy)hydroxyphosphinyloxy]ethyl}-1-methylpiperidinium inner salt; 1-{2-[(11-Adamantylideneundecyloxy)hydroxyphosphinyloxy]ethyl}-1-methylmorpholinium inner salt; 1-{2-[(11-Cyclohexylundecyloxy)hydroxyphosphinyloxy]ethyl}-N,N,N-trimethylammonium inner salt; 1-{2-[(5-Adamantylpentyloxy)hydroxyphosphinyloxy]ethyl}-N,N,N-trimethylammonium inner salt; or 1-{2-[(11-Adamantylundecyloxy)hydroxyphosphinyloxy]ethyl}-N,N,N-trimethylammonium inner salt.

19. The compound of claim 1 wherein:
A is R$^1$OYOR$^2$;
W is R$^3$Q;
X is oxygen;
Y residue is a carbocyclic ring, a substituted carbocyclic ring, a bridged tricyclic ring system, a substituted bridged tricyclic ring system or an aromatic system;
R$^1$ is a C12 to C18 alkyl group;
R$^2$ is a C2 saturated alkyl;
R$^3$ is a C2 saturated alkyl; and
Q is an ammonium group, wherein said ammonium group can be independently substituted one or more times with a C1 to C6 alkyl radical, or is a C3 to C7 heterocycle containing a nitrogen heteroatom which is bonded to the R$^3$ group, wherein said heterocycle can contain one or more heteroatoms independently selected from nitrogen, oxygen or sulfur, and wherein said heterocycle can be substituted with one or more independently chosen substituents.

20. The compound of claim 18 which is selected from 1-{2-{[(4-(Dodecyloxy)cyclohexyloxy)ethyloxy]hydroxyphosphinyloxy}ethyl}-1-methylpiperidinium inner salt, 1-{2-{[(4-(Dodecyloxy)cyclohexyloxy)ethyloxy]hydroxyphosphinyloxy}ethyl}-1-methylmorpholinium inner salt, 1-{2-{[(4-(Tetradecyloxy)cyclohexyloxy)ethyloxy]hydroxyphosphinyloxy}ethyl}-1-methylpiperidinium inner salt, or 1-{2-{[(4-(Tetradecyloxy)cyclohexyloxy)ethyloxy]hydroxyphosphinyloxy}ethyl}-1-methylmorpholinium inner salt.

21. A pharmaceutical composition consisting of a compound of claim 1 and a pharmaceutically acceptable carrier.

22. A method of treating leishmaniasis, trypanosomiasis, malaria, toxoplasmosis, babeosis, amoebic dysentery and lambliasis in an individual or animal in need of treatment, comprising administering an effective amount of a compound of claim 1.

* * * * *